United States Patent [19]

Petty

[11] Patent Number: 4,526,727

[45] Date of Patent: Jul. 2, 1985

[54] PROCESS FOR PREPARATION OF AN S-ALPHA-CYANO S-ALPHA-ISOPROPYLPHENYLACETATE

[75] Inventor: Walter L. Petty, Houston, Tex.

[73] Assignee: Shell Oil Company, Houston, Tex.

[21] Appl. No.: 585,963

[22] Filed: Mar. 5, 1984

Related U.S. Application Data

[63] Continuation-in-part of Ser. No. 460,334, Jan. 24, 1983, abandoned.

[51] Int. Cl.³ .......................................... C07C 121/75
[52] U.S. Cl. ................................................ 260/465 D
[58] Field of Search .................................. 260/465 D

[56] References Cited

U.S. PATENT DOCUMENTS

| | | | |
|---|---|---|---|
| 4,273,727 | 6/1981 | Martel et al. | 260/465 F |
| 4,293,504 | 10/1981 | Suzuki et al. | 260/465 D |
| 4,312,816 | 1/1982 | Abeta et al. | 260/465 D |
| 4,321,212 | 3/1982 | Suzuki et al. | 260/465 D |

*Primary Examiner*—Dolph H. Torrence

[57] ABSTRACT

A method of preparing an "A-alpha" single stereoisomer of an S-alpha-cyano-3-phenoxybenzyl S-alpha-isopropylphenylacetate by precipitation from a solution of an "alpha" diastereoisomer pair, S-alpha-cyano-3-phenoxybenzyl R,S-alpha-isopropylphenylacetate, and optional hydrolysis of the mother liquor and recycle of the components thereof. The phenylacetate "alpha" is prepared from the S-alpha-cyano-3-phenoxybenzyl alcohol and racemic alpha-isopropylphenylacetic acid or reactive derivative thereof.

21 Claims, No Drawings

PROCESS FOR PREPARATION OF AN S-ALPHA-CYANO S-ALPHA-ISOPROPYLPHENYLACETATE

CROSS-REFERENCE TO RELATED APPLICATIONS

This application is a continuation-in-part of Ser. No. 460,334, filed Jan. 24, 1983, abandoned.

BACKGROUND OF THE INVENTION

1. Field of the Invention

This invention relates to a process for the preparation of an "A-alpha" single stereoisomer of an S-alpha-cyano-3-phenoxybenzyl S-alpha-isopropylphenylacetate in substantially pure form or of a mixture enriched in said "A-alpha".

2. Description of the Prior Art

S-alpha-cyano-3-phenoxybenzyl S-alpha-isopropylphenylacetates are of interest because this "A-alpha" isomer has high pesticidal activity as compared to the racemic mixture, any of the diastereoisomer pairs or other single stereoisomer forms of such alpha-cyano-3-phenoxybenzyl alpha-isopropylphenylacetates. While various methods have been proposed to prepare the "A-alpha" isomer, they have had a number of limitations for practical use, e.g. because they have required cumbersome methods of classical resolution of the acid.

SUMMARY OF THE INVENTION

The present invention is directed to a method of preparing a phenylacetate "A-alpha" single stereoisomer of an S-alpha-cyano-3-phenoxybenzyl S-alpha-isopropylphenylacetate in substantially pure form or a mixture enriched in said "A-alpha" single stereoisomer, which comprises treating a solvent solution of a phenylacetate "alpha" isomer mixture, which is a S-alpha-cyano-3-phenoxybenzyl alcohol diastereoisomer pair consisting of S-alpha-cyano-3-phenoxybenzyl R,S-alpha-isopropylphenylacetate, to precipitate crystals of the S-alpha-cyano-3-phenoxybenzyl S-alpha-isopropylphenylacetate and removing said crystals from the mother liquor.

Thus, a phenylacetate "A-alpha" can be precipitated by cooling (crystallizing) a phenylacetate "alpha" at any temperature and pressure at which phenylacetate "A-alpha" crystals form, for example at about −15° C. to about 20° C. and, preferably about −15° C. to about 5° C. The crystalline phenylacetate "A-alpha" is usually recovered in about 65% or higher purity. Further crystallizations yield a product phenylacetate "A-alpha" of purity of at least 75% and usually above at least 80%, or even above 95%. Crystals enriched in phenylacetate "A-alpha" are formed during in situ cooling of phenylacetate "alpha" in a solvent, for example, methanol with or without the addition of phenylacetate "A-alpha" seed crystals.

A second embodiment of the present invention is a process for the preparation of an "A-alpha" single stereoisomer of an S-alpha-cyano-3-phenoxybenzyl S-alpha-isopropylphenylacetate in substantially pure form or of a mixture enriched therein, which comprises treating a racemic alpha-isopropylphenylacetic acid or reactive derivative thereof with an S-alpha-cyano-3-phenoxybenzyl alcohol or a mixture enriched therein to give a phenylacetate "alpha" diastereoisomer pair, precipitating crystals of a S-alpha-cyano-3-phenoxy-benzyl S-alpha-isopropylphenylacetate from the mixture and recovering said crystals.

The reactive derivatives of the racemic alpha-isopropylphenylacetic acid which can be used in the esterification include an acid anhydride, an ester with a low boiling alcohol, an acid halide, especially an acid chloride, and an alkali metal salt, silver salt or an organic tertiary base salt of the acid and the like. The acid chloride is preferred.

The reaction can be conducted in an appropriate inert solvent, preferably a hydrocarbon, such as benzene, toluene, hexane, heptane and the like, at room temperature and, if the acid halide is used, in the presence of a molar excess of an acid acceptor, such as a tertiary amine (pyridine, triethylamine, lutidine, dimethylbenzylamine and the like).

Solvents used in the precipitation process can be any inert material in which the phenylacetate is at least partly soluble at room temperature. Examples of suitable classes of solvents include chlorinated hydrocarbons, ethers, nitriles, esters, amides, hydroxylic solvents and the like. Suitable hydroxylic solvents include lower alkanols containing from 1 to 4 carbon atoms such as isopropanol, butanol, ethanol, and methanol, and preferably containing from 1 to 2 carbon atoms, especially methanol. Other suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between about 40° to about 65° C., between about 60° to about 80° C. or between about 80° to 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, O-, m-and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene. Ethers are generally those containing from 4 to 6 carbon atoms such as diethyl ether, methyl tert-butyl ether and diisopropyl ether. Tetrahydrofuran and dioxane are also useful. Nitriles usually also contain from 2 to 6 carbon atoms, for example, acetonitrile and the like. Esters are those of lower alcohols and acids each containing from 2 to 6 carbon atoms, for example, ethyl acetate. Amides are those of lower alkyl amines and acids each containing from 1 to 6 carbon atoms, for example, dimethylformamide.

While different solvents may be employed in the crystallization and earlier esterification steps, it can be desirable to use the same solvent in both steps, with alkanes (heptanes) or aromatic hydrocarbons (toluene) being preferred. Alkanols containing 1 to 4 carbon atoms, especially methanol, are particularly useful for crystallization.

Precipitation, e.g. crystallization, is conducted by forming a mixture of the "Alpha" in a suitable solvent as defined above. The process can be conducted at any temperature at which crystals enriched in phenylacetate "A-alpha" form, suitably from about −50° to about 60° C., preferably from about −35° to about 5° C. and especially from about −15° to about 5° C.

It is often desirable to add substantial amounts of seed crystals to enhance the rate of crystallization. It is usually most convenient to use crystals of the essentially pure phenylacetate "A-alpha" or crystals enriched therein as seed crystals although crystals of single diastereoisomer phenylacetate "B-beta" (the R,R enantiomer of "A-alpha") can be used. Use of high purity phenylacetate "A-alpha" seed crystals appear to lead to higher yields of phenylacetate "A-alpha". Other known nucleating agents can be used when seed crystals are desired, for example, powdered silica, potassium acetate and the like. The amount of seed crystals used is not critical, but the crystallization is faster with a large amount of seed crystals. The amount of seed crystals may vary from about 0.05 to about 10% based upon the phenylacetate in solution and is preferably about 1%. Of course, as the process progresses, the phenylacetate "A-alpha" crystals being formed also serve as further amounts of seed crystals. The crystals enriched in phenylacetate "A-alpha" produced during the process can be separated and recovered from the crystallization by such methods as filtration, centrifugation or decantation of the mother liquor and the like.

A third embodiment of the present invention is a process for the preparation of an "A-alpha" single stereoisomer of an S-alpha-cyano-3-phenoxybenzyl S-alpha-isopropylphenylacetate, in substantially pure form or of a mixture enriched therein, which comprises treating a racemic alpha-isopropylphenylacetic acid or reactive derivative thereof with an S-alpha-cyano-3-phenoxybenzyl alcohol or a mixture enriched therein to give a phenylacetate "alpha" diastereoisomer pair, precipitating crystals of phenylacetate "A-alpha" single stereoisomer (e.g., S-alpha-cyano-3-pheoxybenzyl S-isopropylphenylacetate) separating these phenylacetate "A-alpha" crystals from the phenylacetate "B-alpha" rich mother liquor, treating the mother liquor to hydrolyze the ester and to recover the corresponding 3-phenoxy-benzaldehyde, and R-alpha-isopropylphenylacetic acid or derivative thereof and hydrogen cyanide.

Hydrolysis of the phenylacetate "B-alpha" is conducted using any conventional hydrolysis procedure which will not cause further conversion of the 3-phenoxybenzaldehyde moiety. One preferred method of hydrolysis is using a mild base, such as lithium hydroxide and the like. The resultant 3-phenoxybenzaldehyde, R-alpha-isopropylphenylacetic acid or derivative thereof and hydrogen cyanide are preferably recovered by conventional techniques and recycled to prepare more of the phenylacetate "alpha", S-alpha-cyano-3-phenoxybenzyl R,S-alpha-isopropylphenylacetate. The R-alpha-isopropylphenylacetic acid or derivative must be racemized to the corresponding R,S-alpha-isopropylphenylacetic acid or derivative in the course of this recovery and recycle process. The R-alpha-isopropyl-phenylacetic acid can be racemized by a variety of conventional techniques known in the art either in the form of the acid, the acid chloride or acid salt. One procedure involves heating the acid to at least 150° C., and preferably above at least 200° C. in the presence or absence of an inert solvent such as a hydrocarbon, halogenated hydrocarbon or the like, preferably in an inert gas such as nitrogen or argon. One of the many alternative procedures, involves treating the acid with aqueous alkali or alkaline earth metal hydroxide or carbonate, e.g. sodium hydroxide, to form the corresponding salt, heating the salt to at least 110° C. to racemize and acidifying the racemic salt to the acid. The acid is then used directly in esterification or converted to the corresponding chloride by treatment with thionyl chloride.

One preferred method of recovery and recycle of the acid is to hydrolyze the recovered lithium salt of R-alpha-isopropylphenylacetic acid, racemizing by treating with, e.g., aqueous alkali metal hydroxide or the like (e.g. sodium hydroxide) with heating of the salt formed, acidifying by conventional methods (e.g. with concentrated hydrochloric acid) to the free acid, and, if desired, treating with thionyl chloride to give racemic R,S-alpha-isopropylphenylacetyl chloride for use in the esterification step. The lithium cyanide is treated by conventional methods to generate hydrogen cyanide, preferably by treatment with an acid, such as sulfuric acid or the like. The hydrogen cyanide and recovered 3-phenoxybenzaldehyde are used in processes to produce the S-alpha-cyano-3-phenoxybenzyl alcohol or a mixture enriched therein. One preferred method is reacting the hydrogen cyanide directly with the 3-phenoxybenzaldehyde in the presence of a cyclo(D-phenylalanyl-D-histidine)dipeptide catalyst (as further described below) to give the corresponding S-alpha-cyano-3-phenoxybenzyl alcohol or a mixture enriched therein for use in the esterification step.

Phenylacetate "alphas" which can be used to prepare their corresponding phenylacetate "A-alpha" products include those having the formula I

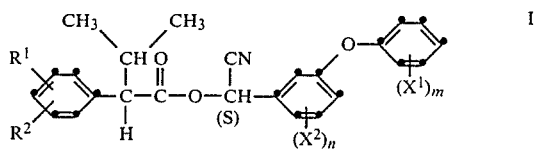

wherein $R^1$ is a hydrogen atom, a halogen atom having an atomic number of from 9 to 53, inclusive, or an alkyl group containing from 1 to 4 carbon atoms or an alkoxy group containing from 1 to 2 carbon atoms, each optionally substituted by one or more halogen atoms having an atomic number of from 9 to 53, inclusive, $R^2$ is a hydrogen atom or a methyl group, $X^1$ and $X^2$ each independently is a halogen atom having an atomic number of from 9 to 35, inclusive, or is methyl and m and n each independently is 0 or 1, and (S) denotes the absolute configuration of the asymmetric carbon atom in the alcohol moiety.

Preferably, $R^1$ is a halogen atom or an optionally halogenated alkyl or alkoxy group as defined above, for example, $R^1$ is a chlorine or fluorine atom, methyl, ethyl, isopropyl, tert-butyl, methoxy, ethoxy, difluoromethoxy or trifluoromethoxy and $R^2$ is a hydrogen atom. $R^1$ is preferably located at the meta- or para-position relative to the benzyl carbon atom in the acid moiety. Preferably, $R^1$ is located at the para-position. Also preferred are those phenylacetates of formula I wherein m is 0 and n is 0 or 1, and $X^2$ is located in the 4-position relative to the benzyl carbon atom in the alcohol moiety. Especially useful are those phenylacetates of formula I wherein n is 0 or when n is 1 then $X^2$ is fluorine at the 4-position. It is further preferred to prepare a phenylacetate "A-alpha" product of a material of formula I in which $R^1$ is chlorine or difluoromethoxy, $R^2$ is a hydrogen atom, $X^2$ is fluorine and m is 0 and n is 0 or 1.

The alpha-isopropyl-phenylacetic acids and reactive derivatives thereof are generally known as in U.S. Pat. Nos. 3,996,244 and 4,199,595. They are hydrolyzed from their lithium salts during the process of the invention by conventional acid or base hydrolysis processes for carboxylic acid salts, e.g. with mineral acids or the like.

The S-cyano alcohols or a mixture enriched therein can be prepared by the method of U.S. Pat. No. 4,273,727 from the corresponding racemic alcohols or for example, the S-alpha-cyano-3-phenoxybenzyl alcohols or a mixture enriched therein are conveniently prepared from the corresponding aldehyde which is treated with a source of hydrogen cyanide in a substantially water-immiscible, aprotic solvent and in the presence of a cyclo(D-phenylanyl-D-histidine)dipeptide catalyst. This process is described in an earlier commonly assigned U.S. patent application, Ser. No. 443,763, filed Nov. 22, 1982, now abandoned in favor of continuation-in-part Ser. No. 551,548, filed Nov. 14, 1983, and also in Ser. No. 535,500, filed Sept. 26, 1983, and discussed below.

A substantially water-immiscible, aprotic solvent for use in the preparation of the S-cyano alcohols with the dipeptide catalyst is defined as an aprotic solvent in which the solubility in water is not more than 5%v (and does not interfere with the reaction). For example, the solvent is a hydrocarbon, chlorinated hydrocarbon or ether solvent including acyclic, alicyclic or aromatic materials. Preferably, at the reaction temperature the solvent has a boiling point below about 150° C. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Useful ethers include diethyl ether, diisopropyl ether, methyl-t-butyl ether and the like. Preferably, the solvent is an aromatic hydrocarbon, especially toluene, diisopropyl ether or diethyl ether or mixtures thereof (e.g. 25/75 of diethyl ether/toluene).

The source of cyanide ions is conveniently usually recycle hydrogen cyanide. The molar ratio of hydrogen cyanide to aldehyde or ketone is from about 1.0 to about 3.0 and, preferably, from about 1.1 to about 2.0.

The catalyst is prepared by conventional peptide synthesis, for example, as in Greenstein, J. P. and M. Winitz, "Chemistry of the Amino Acids", John Wiley & Sons, Inc., New York, 1961. They can be recovered by extraction with acid followed by neutralization with a base.

In one embodiment of the process for preparing the S-cyano alcohols, the catalyst comprises a solid cyclo(D-phenylalanyl-D-histidine) having a substantially non-crystalline component as claimed in copending U.S. Ser. No. 535,500, filed Sept. 26, 1983, and also described below.

In other words, the catalyst has a component having a substantially amorphous or non-crystalline structure. While the precise form of this cyclo(D-phenylalanyl-D-histidine)dipeptide is not known, it appears that in the activated (amorphous or non-crystalline) form, a number of the available —NH groups in the dipeptide are free of intermolecular hydrogen bonding to the available —C═O groups of the dipeptide crystal lattice as compared to the less active (crystalline component) form. This is believed to involve the formation of a less bonded linear or planar (or sheet) form of peptide structure as opposed to the highly bonded ribbon (or chain) form of peptide structure because of the increase in the number of —NH groups free of intermolecular hydrogen bonding to available —C═O groups in the dipeptide lattice. Such being the case, the degree of amorphousness or non-crystallinity is most readily determined by X-ray diffraction.

The wide-angle X-ray scattering (WAXS) measurements were carried out in reflection by means of a Philips APD3600/02 automated X-ray diffractometer. The samples were scanned at 20° C. in air from 5.0° to 60.0° $2\theta$ at 0.02 degree increments, and 0.6 second time increments with Cu K$\alpha$ radiation (40 KV, 35 ma).

The percent crystallinity was determined by a modified Hermans and Weidinger method (P. H. Hermans and A. Weidinger, *Makromol. Chem.*, 50, 98 (1961)). The diffuse background scattering below the main peaks was constructed assuming a linear baseline between $5° < 2\theta < 60°$ and approximating the amorphous scattering with a smooth curve. The X-ray crystallinity, $W_c$, was calculated from the integrated crystalline and amorphous intensities $F_c$ and $F_a$ by the equation $W_c = F_c/(F_c + F_a)$. The various definitions can be found in the text H. P. Klug and L. E. Alexander, *X-Ray Diffraction Procedures for Polycrystalline and Amorphous Materials*, Wiley-Interscience, New York, (1974).

As used herein the terms "amorphous" or "non-crystalline" define active catalyst materials which have about 20% or more of an amorphous or non-crystalline component as determined by the area of the X-ray diffraction spectra obtained by the method described above. Preferably, the "amorphous" or "non-crystalline" component of the materials as defined by the X-ray diffraction spectra is about 45% to about 65% or higher. Preferably, the "amorphous" or "non-crystalline" component is about 65% or higher.

The catalysts are also analyzable by photomicrographs in which inefficient catalysts consist of agglomerates of fine crystallites. Crystallites are not evident in photomicrographs of active catalysts, which when, for example, are spray-dried, take the form of hollow-appearing spheres.

The solid catalyst can be recovered by extraction with acid followed by neutralization with a base or preferably by treating with (dissolving in) a solvent, for example a hydroxylic solvent, including lower alkanols of 1 to 10 carbon atoms such as isopropanol or preferably methanol (preferably with heating, e.g. to reflux or quick flash), and reprecipitating (preferably below ambient temperature) which produces a less crystalline (or more amorphous) catalyst structure.

While it is preferred to directly prepare the catalyst of the present invention having the non-crystalline component, it is also within the scope of this invention to prepare a substantially crystalline catalyst and to subsequently activate the catalyst by converting at least part of the crystalline material to an amorphous form. Thus, the present invention is directed to both a method of directly preparing an active cyclo(D-phenylalanyl-D-histidine)dipeptide catalyst and to a method of activating a crystalline catalyst of this type, which methods both involve reducing or preventing the formation of a substantially crystalline form thereof. In the case of activation of a crystalline catalyst, the crystalline form is first broken down and then prevented at least in part from reforming.

It is believed that the breakdown of or the prevention of the formation of a number of intermolecular bonds between the amino N—H and the carboxyl C=O groups in the crystal lattice makes the catalyst have an amorphous or non-crystalline form. In any event, an ordered deposition of crystals of the catalyst is discouraged or reduced.

Any means which will accomplish this reduction or prevention either during the catalyst preparation or an after treatment are within the scope of the invention. Among the illustrative examples of methods which reduce or prevent the formation of a highly crystalline form or highly ordered arrangement are (a) very rapid evaporation of a solution of the catalyst, in the presence or absence of impurities or crystallinity inhibitors; (b) rapid precipitation of the catalyst from solution by dilution in a poor solvent; (c) freeze drying of a solution of the catalyst; (d) rapid cooling of the melted catalyst in the presence or absence of impurities or crystallinity inhibitors; (e) use of crystallinity inhibitors during solidification; and the like.

The unactivated dipeptide catalyst, when recovered at the end of a conventional synthesis process, is often almost completely inactive in the cyanohydrination reaction, apparently because it has become highly crystalline as can be determined by X-ray diffraction. Activation, as used herein, appears to involve converting at least part of the normally crystalline material into an amorphous form such that the dipeptide is swelled by the reaction mixture and the chiral base function of the catalyst is made accessible to the reactants. In order to produce high chirality in the cyanohydrination product, it appears that the catalyst should preferably be essentially insoluble in the cyanohydrination solvent.

The first step in converting what is or what normally would be a crystalline material to an amorphous form is to break down (or prevent) formation of the intermolecular bonds in the crystal lattice. The breakdown readily occurs when the material is melted or dissolved in a solvent. Once this has been accomplished, a method is used that will allow the separation of the dissolved material from the solvent at a rate such that normal crystallization cannot occur. There are a number of ways in which this might be effected: (a) rapid evaporation of the solvent, e.g. as in a spray drier; (b) rapid precipitation of the material by pouring a solution of it into a large volume of a different solvent that is miscible with the original solvent but does not dissolve, to a large extent, the material to be precipitated; (c) rapid freezing of a solution followed by sublimation of the solvent (freeze drying); (d) rapid cooling of the melted catalyst; and (e) use of inhibitors alone or with any of the above methods (a)–(d). Preferably, the method used is (a) rapid evaporation of the solvent and, especially, by means of spray drying.

Because of the polar nature and high melting point (~250° C.) of cyclo(D-phenylalanyl-D-histidine), the choice of solvents that will dissolve it to any appreciable extent is very limited. Potential solvents suitable and unsuitable that have been tested include those listed in Table 1 in order of decreasing effectiveness, and the use of these will be discussed below in relation to the method of catalyst activation via recovery techniques or specific subsequent activation treatment.

TABLE 1

SOLVENTS TESTED FOR SOLUBILITY OF CYCLO(D-PHENYLALANYL-D-HISTIDINE)

| Solvent | B.P./°C. | Solvency |
|---|---|---|
| Dimethyl Sulfoxide | 189 | Good (5–10% w) |
| Acetic Acid | 118 | Good |
| Formamide | 210 | >2.3% at 25° C. |
| 1-Methyl-2-pyrrolidinone | 202 | >2.2% at 25° C. |
| Dimethylformamide | 153 | Fair to Good, <5% at 90° C. |
| Liquid Ammonia | −33 | ~2% at −40° C. |
| N—methylformamide | 185 | >2.4% at 25° C. |
| Methanol | 64 | 1% w Hot, 0.3% w at 25° C. |
| Water | 100 | Fair to Poor, 0.1% at 25° C. |

The use of crystallization inhibitors is an alternative method of reducing or preventing the crystalline form of the dipeptide. Many chemicals can be used. It is useful if the crystallization inhibitor has a similar kind of structure or has one or more substituents similar in kind to those found in the dipeptide, but the inhibitor is not identical to the units of the dipeptide. In the case of this dipeptide, useful kinds of crystallization inhibitors include those materials containing a —N—H and/or —C=O group, including ureas, aldehydes and amines. Even by-product impurities of the dipeptide process containing such substituents are useful crystallization inhibitors, e.g. making an impure product can make a more active catalyst.

When the catalysts are prepared by conventional methods in the presence of water, they can, if solid, also contain solvent (e.g. water) of crystallization. The dipeptide catalyst thus includes the presence or absence of solvent (e.g. water) of crystallization when solid.

The amount of catalyst used in making the S-cyano alcohols can vary. For example, it can be used in the range of from about 0.1 to about 10 mole percent based upon the weight of the aldehyde present, preferably about 1.0 to about 7.5 mole percent. The catalyst is preferably well dispersed in the reaction mixture.

The reaction to prepare the S-cyano alcohols is suitably conducted by adding the benzaldehyde and solvent to the dipeptide catalyst, dispersing (mechanical grinding or agitating the mixture, e.g. by stirring), adding hydrogen cyanide and maintaining the reaction conditions for an amount of time to effect the formation of the S-cyano alcohol. That is, preferably, the hydrogen cyanide is introduced concurrently with, subsequent to or rapidly followed by the solvent and/or aldehyde to increase the conversion and stereoselectivity. The presence of cyanide ions has an adverse effect on the catalyst in this reaction and competing racemization is reduced by protecting the catalyst from cyanide ions. The forming and maintaining of a well dispersed but not necessarily homogeneous-like reaction mixture are useful. Separation and recovery of the S-cyano alcohol product are achieved by conventional techniques, including extraction and the like.

The temperature of the reaction to prepare the S-cyano alcohols as well as the pressure can vary. At normal pressures, the temperature is from about 0° C. to about 80° C., more or less. Preferably, ambient temperatures of about 15° C. to about 35° C. are convenient to give good yield, rate of reaction and enantiomeric excess of the desired optically-active product, the lower temperature of 5° C. giving good results.

PREFERRED EMBODIMENT OF THE INVENTION

In the preferred embodiment, any of the above procedures are conducted to prepare the single steroisomer, S-alpha-cyano-3-phenoxybenzyl S-alpha-isopropyl-p-chlorophenylacetate, or a mixture enriched therein. For example, the present invention provides a process for preparing the single stereoisomer, S-alpha-cyano-3-phenoxybenzyl S-alpha-isopropyl-p-chlorophenylacetate, (hereinafter referred to as fenvalerate "A-alpha") which process comprises precipitating crystals of fenvalerate "A-alpha" optionally in the presence of crystals of fenvalerate "A-alpha" from a solution of the diastereoisomer pair consisting of S-alpha-cyano-3-phenoxybenzyl S-alpha-isopropyl-p-chlorophenylacetate and S-alpha-cyano-3-phenoxybenzyl R-alpha-isopropyl-p-chlorophenylacetate, separating the fenvalerate "A-alpha" crystals from the mother liquor, (optionally treating the mother liquor solution of fenvalerate B-alpha as previously described for phenylacetate "B-alphas") and recovering fenvalerate "A-alpha" from the mother liquor.

While the various reaction conditions and solvents previously described above for the phenylacetate "alphas" can be employed to prepare fenvalerate "alpha", it is preferable to employ toluene or heptane as the solvent for the preparation and then an alkanol containing from 1 to 4 carbon atoms for the precipitation (crystallization), with the use of methanol preferred.

As mentioned earlier, the product fenvalerate "B-alpha" enriched mother liquor is separated from the fenvalerate "A-alpha" or "A-alpha" enriched crystals by known methods, for example, by centrifuging off the fenvalerate "A-alpha" or "A-alpha" enriched crystals. The fenvalerate "B-alpha" mother liquors can be treated for recycle as previously described for phenylacetate "B-alpha".

It will be appreciated by those skilled in the art that the present process can be conducted as a batch, semi-continuous or continuous process employing one or more treatment vessels as appropriate.

ILLUSTRATIVE EMBODIMENTS

The invention is also described by the following embodiments which are for the purpose of illustration only and should not be regarded as limiting the invention in any way.

EMBODIMENT I

A solution of 240 g of S-alpha cyano-3-phenoxybenzyl R,S-alpha-isopropyl-p-chloro-phenylacetate, 4.49 g of potassium acetate (an optional nucleating agent), and 520 g of methanol is cooled to below 0° C. Crystals begin to grow. This mixture is allowed to stand at room temperature for several hours. Then the mixture is shaken to break-up chunks of solid and filtered. The recovered white solid is rinsed with ice-cold methanol to give a mixture enriched in S-alpha-cyano-3-phenoxybenzyl S-alpha-isopropyl-p-chlorophenylacetate. The enriched mixture is recrystallized about 3 times from methanol, acidified with acetic acid, to give a phenylacetate "A-alpha", S-alpha-cyano-3-phenoxybenzyl S-alpha-isopropyl-p-chlorophenylacetate, of purity in excess of 95% and a melting point of 60° C.

EMBODIMENT II

A mixture of 6 g of S-alpha-cyano-3-phenoxybenzyl alcohol, 6.2 g of racemic alpha-isopropyl-p-chlorophenylacetyl chloride and 50 ml of toluene is cooled to 15° C. and then a mixture of 8 ml of pyridine in 20 ml of hexane is added dropwise. The mixture is stirred at 20° C. for several hours, poured into 2N aqueous hydrochloric acid, the decanted organic phase dried and filtered and the filtrate evaporated under reduced pressure. The residue is optionally chromatographed over silica gel to obtain a phenylacetate "alpha", S-alpha-cyano-3-phenoxybenzyl R,S-alpha-isopropyl-p-chlorophenylacetate, as a viscous liquid. The liquid is dissolved in 30 ml of methanol and cooled below 0° C. After several hours, the crystals which form are worked up as described in Embodiment I above to obtain S-alpha-cyano-3-phenoxybenzyl S-alpha-isopropyl-p-chlorophenylacetate of purity in excess of 95% and a melting point of 60° C.

EMBODIMENT III

To a mixture of 250 g of racemic R,S-alpha-isopropyl-p-chlorophenyl-acetyl chloride in 400 ml of heptane is added a solution of 225 g of S-alpha-cyano-3-phenoxybenzyl alcohol in 200 ml of heptane at −10° C. and then a solution of a molar excess of pyridine (based on the acid chloride) in heptane. The mixture is maintained at 20° C. for 24 hours, washed with dilute hydrochloric acid, then with sodium bicarbonate solution, dried and evaporated to dryness. The residue is optionally chromatographed over silica gel to obtain a phenylacetate "alpha", S-alpha-cyano-3-phenoxybenzyl R,S-alpha-isopropyl-p-chlorophenylacetate, as a viscous liquid. A solution of this phenylacetate "alpha" is dissolved in methanol, cooled to below 0° C. and seeded with crystals of the "A-alpha" isomer. After the crystals begin to form, the mixture is allowed to stand at room temperature for several hours, then the mixture is agitated to break-up the solids, and filtered. The phenylacetate "B-alpha" containing filtrate is treated with excess lithium hydroxide to hydrolyze the phenylacetate "B-alpha" rich mother liquor to the corresponding 3-phenoxybenzaldehyde and the lithium salts of alpha-isopropyl-p-chloroacetic acid and cyanide. The acid (from hydrolysis of the lithium salt) is racemized by heating with aqueous sodium hydroxide, then acidified and treated with thionyl chloride to give racemic R,S-alpha-isopropyl-p-chlorophenylacetyl chloride which is recycled to the esterification step. The cyanide ions are recovered by conventional techniques as hydrogen cyanide and is used with the recovered 3-phenoxybenzaldehyde to prepare the S-alpha-cyano-3-phenoxybenzyl alcohol in the presence of a cyclo(D-phenylalanyl-D-histidine) catalyst. The crystals of "A-alpha" are washed with methanol and recrystallized from methanol about five times to give S-alpha-cyano-3-phenoxybenzyl S-alpha-isopropyl-p-chlorophenylacetate of at least 95% purity as a white solid, melting point 60° C.

EMBODIMENT IV

A 100 ml three-neck Bantam ware flask was charged with 43 mg of cyclo(D-phenylalanyl-D-histidine) and put under a nitrogen atmosphere. Then, 3.51 ml of hydrogen cyanide was added by syringe causing the catalyst to swell and become a gel. After 5 minutes, 30 ml of toluene was added, causing additional catalyst to precipitate. 5.95 g of 3-phenoxybenzalde-hyde was added all at once. The reaction mixture was stirred for 4.75 hours and then quenched with 20 ml of water containing 10 drops of concen-trated hydrochloric acid. The toluene solution was separated, washed twice with water, diluted to 50 ml with toluene for analysis, which showed 80% S-alpha-cyano-3-phenoxybenzyl alcohol isomer was produced. This product is optionally treated as described in U.S. Pat. No. 4,273,727.

A sample of the above S-alcohol is treated with racemic R,S-alpha-isopropyl-p-chlorophenylacetyl chloride in the presence of pyridine to obtain S-alpha-cyano-3-phenoxybenzyl, R,S-alpha-isopropyl-p-chlorophenylacetate.

What is claimed is:

1. A method of preparing a phenylacetate "A-alpha" single stereoisomer of an S-alpha-cyano-3-phenoxybenzyl S-alpha-isopropylphenylacetate in substantially pure form or of a mixture enriched in said "A-alpha" single stereoisomer, which comprises treating a solvent solution of a phenylacetate "alpha" isomer mixture, which is a diastereo-isomer pair consisting of S-alpha-cyano-3-phenoxybenzyl R,S-alpha-isopro-pylphenylacetate, to precipitate crystals of the S-alpha-cyano-3-phenoxy-benzyl S-alpha-isopropylphenylacetate and removing said crystals from the mother liquor.

2. A method for the preparation of an "A-alpha" single stereoisomer of an S-alpha-cyano-3-phenoxybenzyl S-alpha-isopropylphenylacetate in substantially pure form or of a mixture enriched therein, which comprises treating a racemic R,S-alpha-isopropylphenylacetic acid or reactive derivative thereof with an S-alpha-cyano-3-phenoxybenzyl alcohol or a mixture enriched therein to give a phenylacetate "alpha" isomer mixture, precipitating crystals of an S-alpha-cyano-3-phenoxy-benzyl S-alpha-isopropylphenylacetate from the mixture and recovering said crystals.

3. A method according to claim 2 wherein the "alpha" isomer diastereoisomer pair is prepared from the acid chloride.

4. A method according to claim 2 wherein the phenylacetate "B-alpha" mother liquors from the precipitation are hydrolyzed in the presence of a mild base.

5. A method according to claim 2 wherein the S-alpha-cyano-3-phenoxybenzyl R,S-alpha-isopropylphenylacetate has a formula I

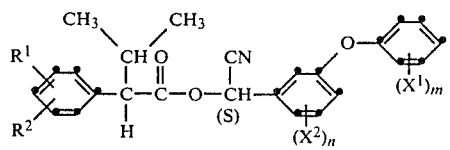

wherein $R^1$ is a hydrogen atom, a halogen atom having an atomic number of from 9 to 53, inclusive, or an alkyl group containing from 1 to 4 carbon atoms or an alkoxy group containing from 1 to 2 carbon atoms, each optionally substituted by one or more halogen atoms having an atomic number of from 9 to 53, inclusive; $R^2$ is a hydrogen atom or a methyl group; $X^1$ and $X^2$ each independently is a halogen atom having an atomic number of from 9 to 35, inclusive, or is methyl; m and n each independently is 0 or 1 and (S) denotes the absolute configuration of the asymmetric carbon atom in the alcohol moiety.

6. A method according to claim 5 wherein the solvent in the precipitation is a hydroxylic solvent.

7. A method according to claim 6 wherein the solvent is a lower alkanol containing from 1 to 4 carbon atoms.

8. A method according to claim 7 wherein the solvent is a lower alkanol containing from 1 to 2 carbon atoms.

9. A method according to claim 7 wherein the solvent is methanol.

10. A method according to claim 4 wherein the base is lithium hydroxide.

11. A method according to claim 5 wherein the precipitation of crystals of phenylacetate "A-alpha" is conducted with the addition of seed crystals of phenylacetate "A-alpha".

12. A method according to claim 11 wherein the precipitation of crystals of phenylacetate "A-alpha" is conducted with the addition of from about 0.05 to about 10% of seed crystals of phenylacetate "A-alpha" based upon the phenylacetate in solution.

13. A method according to claim 9 wherein the precipitation of crystals of phenylacetate "A-alpha" is conducted with the addition of about 1% of seed crystals of phenylacetate "A-alpha" based upon the phenylacetate in solution.

14. A method according to claim 9 wherein in the compound of formula I, $R^1$ is a halogen atom or an optionally halogenated alkyl or alkoxy group; $R^2$ is a hydrogen atom; $X^2$ is 4-fluoro, m is 0; n is 0 or 1, and $R^1$ is at the para-position relative to the benzyl carbon atom in the acid moiety.

15. A method according to claim 14 wherein in the compound of formula I, $R^1$ is chlorine or difluoromethoxy and n is 0.

16. A method according to claim 15 wherein $R^1$ is chlorine.

17. A method according to claim 4 wherein the R-alpha-isopropylphenylacetic acid or derivative thereof is recovered, racemized to the corresponding R,S-alpha-isopropylphenylacetic acid or reactive derivative thereof.

18. A method according to claim 4 wherein hydrogen cyanide and the 3-phenoxybenzaldehyde are recovered and reacted to give the corresponding S-alpha-cyano-3-phenoxybenzyl alcohol or a mixture enriched therein.

19. A method according to claim 18 wherein the reaction to prepare the S-alpha-cyano-3-phenoxybenzyl alcohol or a mixture inriched therein is conducted in the presence of a substantially amorphous or non-crystalline optically-active histidine-containing cyclo(D-phenylalanyl-D-histidine)dipeptide catalyst.

20. A method according to claim 18 wherein S-alpha-cyano-3-phenoxybenzyl alcohol or a mixture enriched therein is treated with R,S-alpha-isopropylphenylacetic acid or reactive derivative thereof to give the corresponding S-alpha-cyano-3-phenoxybenzyl R,S-alpha-isopropylphenylacetate for recycle to the precipitation.

21. A method for the preparation of an "A-alpha" single stereoisomer of an S-alpha-cyano-3-phenoxybenzyl S-alpha-isopropylphenylacetate, in substantially pure form or of a mixture enriched therein, which comprises treating a racemic alpha-isopropylphenylacetic acid or reactive derivative thereof with an S-alpha-cyano-3-phenoxybenzyl alcohol or a mixture enriched therein to give a phenylacetate "alpha" diastereoisomer pair, precipitating crystals of phenylacetate "A-alpha" single stereoisomer, separating these phenylacetate "A-alpha" crystals from the phenylacetate "B-alpha" rich mother liquor, treating the mother liquor to hydrolyze the ester and recovering the corresponding 3-phenoxybenzaldehyde, R-alpha-isopropylphenylacetic acid or derivative thereof and hydrogen cyanide.

* * * * *